United States Patent [19]

Kwon et al.

[11] Patent Number: 5,143,069
[45] Date of Patent: Sep. 1, 1992

[54] DIAGNOSTIC METHOD OF MONITORING SKELETAL DEFECT BY IN VIVO ACOUSTIC MEASUREMENT OF MECHANICAL STRENGTH USING CORRELATION AND SPECTRAL ANALYSIS

[75] Inventors: Seo J. Kwon, Worcester, Mass.; J. Lawrence Katz, Shaker Hgts., Ohio

[73] Assignee: Orthosonics, Inc., New York City, N.Y.

[21] Appl. No.: 562,252

[22] Filed: Aug. 3, 1990

Related U.S. Application Data

[63] Continuation of Ser. No. 342,655, Apr. 24, 1989.

[51] Int. Cl.$^5$ ............................................. A61B 8/00
[52] U.S. Cl. ........................... 128/660.01; 128/660.06
[58] Field of Search ...................... 128/660.01, 660.02, 128/660.06, 661.03; 73/597, 599

[56] References Cited

U.S. PATENT DOCUMENTS 4,941,474  7/1990  Pratt, Jr. .

Primary Examiner—Francis Jaworski
Attorney, Agent, or Firm—Michael Y. Epstein

[57] ABSTRACT

A diagnostic method for determining in vivo mechanical strength and structural integrity of hard tissues such as bones, in a non-invasive and non-dramatic manner. The method separates ultrasound energy affected by surrounding soft tissues, and thus permits unbiased determination of ultrasound parameters that represent the hard tissues. The mechanical strength of hard tissues is then determined on the basis of the ultrasound parameters, including the amount of energy propagated, the velocity of the ultrasound and the degree of dispersion together with the characteristic response of the hard tissues.

9 Claims, 4 Drawing Sheets

DIAGNOSTIC METHOD OF MONITORING SKELETAL DEFECT BY IN VIVO ACOUSTIC MEASUREMENT OF MECHANICAL STRENGTH USING CORRELATION AND SPECTRAL ANALYSIS

This application is a continuation of Ser. No. 342,655 filed Apr. 24, 1989, and now abandoned, which is a continuation of Ser. No. 118,465 filed Nov. 9, 1987, and now abandoned.

BACKGROUND OF THE INVENTION

1. Field of Invention

The present invention relates generally to a diagnostic method of monitoring skeletal defects using low energy pulsed ultrasound. More particularly, the present invention relates to a novel method of separating the effects of soft tissues from those of hard tissues (for example, bone, tendons, cartilage or implanted material) on ultrasound propagation by using correlation analysis and spectral estimation, and by relating the velocity of the propagated ultrasound with the in vivo mechanical strength and structural integrity of hard tissues and in particular of load carrying hard tissues.

Management of patients with bone fractures is currently based on subjective impressions gained by physical examinations and x-ray radiographs taken during various stages of healing. Similarly, patients with bone diseases such as osteoporosis or those with microfractures are apt to be diagnosed solely on subjective impressions in the early stages, due to the limitations of standard radiographic techniques. Even after making a diagnosis based on experience, a physician will generally have to manage a patient conservatively before returning the patient to normal activity. The main reason for the delayed diagnosis in such bone disorders is that currently available diagnostic methods do not objectively access the mechanical strength and structural integrity of hard tissue such as bone, and thus do not provide any substantive failure risk analysis.

2. Description of the Related Art

Two general diagnostic methods are used to diagnose bone disorders. A first method employs ionizing radiation that essentially measures bone mineral density. This first method includes conventional and substrative x-ray imaging, single and dual photon absorptiometry, radio nuclide imaging, and CAT scans. While this first general method of diagnostic method has proven satisfactory for many uses, it has some inherent disadvantages. First repeated and/or excessive exposure to ionizing radiation is harmful to health and causes various kinds of cancer. Accordingly, a diagnostic method based on ionizing radiation cannot be used for frequent applications such as screening, especially of woman of child bearing age. Second, methods such as these are only sensitive to mineral density changes and not to the mechanical strength of hard tissues. Consequently such diagnostic methods generally do not provide information indicating when a bone is at risk of fracture. Third, the cost of diagnostic systems employing such methods significantly increases with the sophistication of the method. This causes economic burden on patients and limits their access to treatment.

The second general method of diagnostic method utilizes some sort of mechanical input to the bone and analyzes the response of the hard tissues. Depending on the kind of mechanical input, this second method can be generally categorized as an impact method, a conventional ultrasound method, or an acoustic emission method. This method of diagnostic system has definite advantages over ionizing radiation based methods because it provides direct information about the mechanical properties of bone, without harmful side effects. However, wide acceptance and clinical usage has not yet occurred. Two drawbacks contributing to the lack of wide clinical usage are the difficulty in controlling the input (e.g. ultrasound) and distortions in the received responses. These difficulties arise due to the effects of adjacent bones, muscles, ligaments and associated soft tissues on input to the bone and the reception of responses. In addition, this method, prior to the present invention, does not solve the problem of soft tissue effect on responses.

It is believed that the present invention will serve as a valuable adjunct to the diagnostic methods currently available and will probably shorten or prevent the disability of many patients. Further, this invention will provide valuable information about the efficacy of various methods of treating particular fractures and provide early diagnosis of bone diseases.

SUMMARY OF THE INVENTION

An object of the present invention is to provide a novel method of quantitative and sensitive measurement of in vivo mechanical strength of hard tissues, unaffected by surrounding soft tissues, in a non-invasive and non-traumatic manner, producing virtually no harmful side effects.

Another object of the present invention is to relate the velocity, the attenuation and the degree of dispersion in distribution of propagated ultrasound energy along the bone to the mechanical strength and structural integrity of that bone.

One of the principal advantages of the present invention is that the correlated output signal is in the most useful form for use in conjunction with diagnosing bone disorders. The invention produces a distribution of transmitted energy peaks having magnitudes and degrees of dispersion that correspond to mechanical strength and structural integrity, and delay times of signals produced and received in accordance with the present invention that correspond to the velocities of ultrasound in particular propagation paths.

Another advantage of the present invention is that use of a fixed reference signal and an additional reference signal eliminate the necessity of using contralateral bone to obtain a base line comparison in monitoring fracture healing. The additional reference signal is established by monitoring the ultrasound propagated along an undamaged part of the bone.

Still another advantage of the present invention is that it is non-invasive, non-traumatic, and produces no harmful side effects. Thus, it can be used as a screening device for diseases or used as a device for monitoring the healing process of fractures, especially in women of child bearing age.

Still another advantage of the present invention is that through proper signal processing, the characteristic response of a bone can be approximated. This approximation provides unbiased information about the status of mechanical strength of the bone, and makes the response of the bone to other mechanical inputs predictable.

The present invention utilizes both the velocity and the attenuation characteristics of ultrasound in hard tissues, and distinguishes these from the corresponding characteristics of soft tissues. A significant feature of this invention lies in its novel method of sorting the ultrasound energy propagated along the bone and other tissues according to the delay time of propagation. Specifically, the sorting can be achieved by establishing a fixed reference signal and correlating it with signals that are propagated through both the hard and soft tissues. Since the present invention separates the responses of soft tissues from the responses of hard tissues, the invention is also well suited for diagnosing soft tissue trauma.

A preferred embodiment of the method of the present invention includes the steps of: (a) mounting spaced apart ultrasound transducers over the skin and propagating an ultrasound signal along the hard tissues and surrounding soft tissues; (b) establishing a fixed reference signal for the ultrasound transducers; (c) receiving a propagated ultrasound signal; (d) sorting the received propagating ultrasound signal according to a relative propagation delay time by correlating the received ultrasound signal with the fixed reference signal; (e) determining a velocity, a propagation energy and a degree of dispersion of the ultrasound signal propagated along the hard tissues and the surrounding soft tissues based upon the propagated ultrasound distribution of step (d); and (f) relating the velocity, propagated energy and degree of dispersion to the mechanical strength and the structural integrity of the hard tissues.

These and other objectives and advantages of the present invention will be more readily apparent from consideration of the following detailed description of the present invention.

DESCRIPTION OF THE PREFERRED EMBODIMENT

Figure 1:
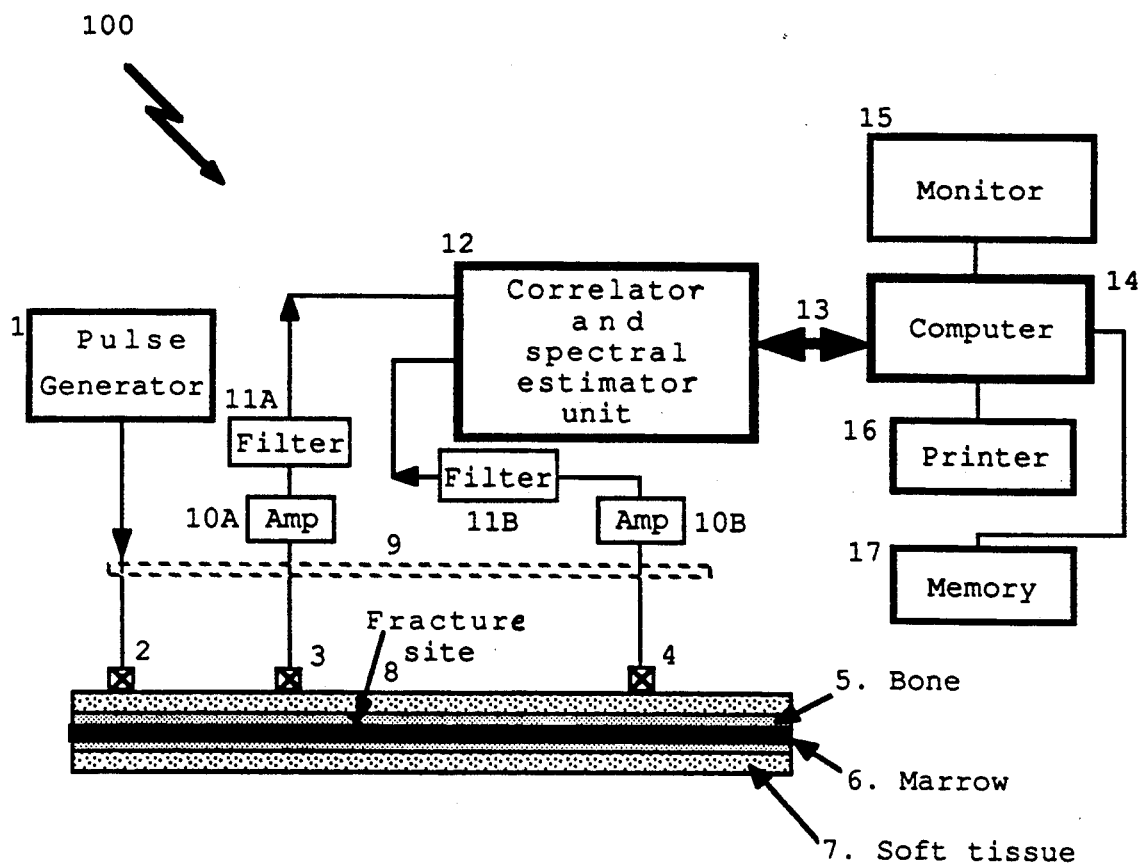
FIG. 1 is a diagram representing the present invention for separating the ultrasound energy propagated through skeletal tissues, and for measuring the velocity and attenuation of ultrasound along an in vivo bone. The bone and surrounding soft tissues are represented diagrammatically in a side view.

Referring to FIG. 1, a resonance type piezoelectric transducer 2, excited by a pulse generator 1, comprise an ultrasound generating system. The transducer 2 is a wide band type, having a bandwidth of, for example, greater than 100 KHz and a resonance frequency of less than 1 MHz, a wide divergence angle (e.g., 90°). The transducer 2 functions as a transmitter. The divergence angle of a transducer is the angle from the center axis of the transducer to the outer boundary of the ultrasound wave front. The divergence angle of a transducer is a function of the wavelength $\lambda$ of the ultrasound in soft tissues and the diameter of the transducer d, such that:

Divergence angle $= (2.23) \sin^{-1}(\lambda/d)$.

Because a bone 5, soft tissues 7 and marrow 6 are each heterogeneous and anisotropic and have complicated geometries, an ultrasound signal is reflected, refracted, and attenuated at the interface boundaries of different densities as it propagates along the bone and the soft tissues.

Figure 2:
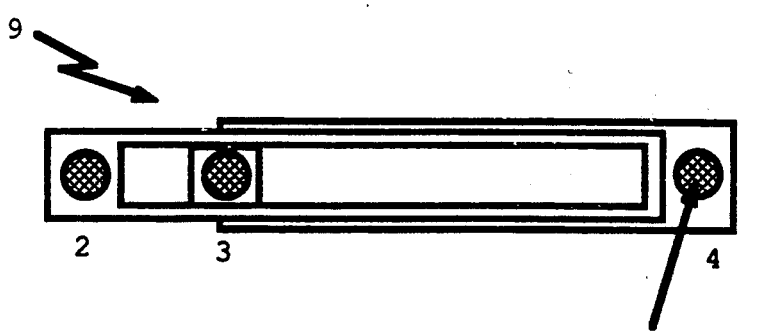
FIG. 2 is a diagrammatic top view representation of a portion of the FIG. 1 system.

Two transducers 3 and 4, which are identical to the transducer 2, are used as receivers. The transducer 3 serves as a reference for a normal portion of a bone, and is mounted closer to the transmitter 2 than the transducer 4 which is located across a suspected defect or fracture site 8. The transducers are mechanically interconnected to determine a distance indicated by 9 in FIG. 1 and FIG. 2, and are mounted over the skin by employing a gel couplant.

Amplifiers 10A, 10B and filters 11A, 11B condition the received signals which are then applied to a signal processing unit 12. The processed signals provided by signal processing unit 12 are sent to a computer 14 via a communication port 13. The computer 14 controls the signal processing procedures, displays processed data on a monitor 15, produces hard copies on a printer 16, and stores data in an external memory device 17 for later analysis.

Figure 3:
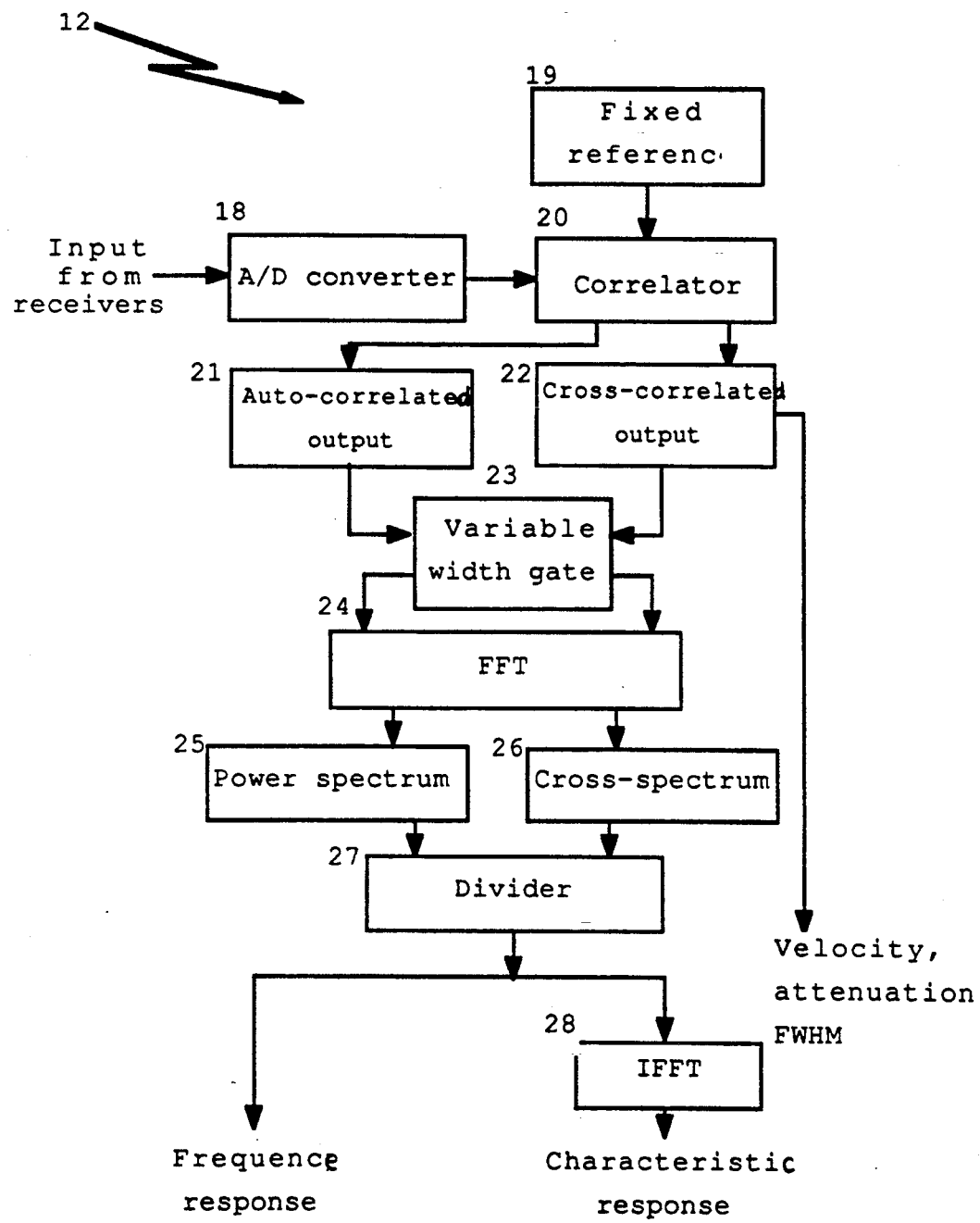
FIG. 3 is a block diagram of a preferred procedure for signal conditioning, correlation analysis and spectral estimation of the present invention.

As shown in FIG. 3, an analog-to-digital converter 18 digitizes ultrasound signals. A fixed reference signal 19 is generated by joining the transmitter 2 and one of the receivers 3 or 4 face to face and is stored in a memory (not shown). A digital correlator 20 calculates an auto-correlation 21 of the received ultrasound signals and a cross-correlation 22 of the received ultrasound signal using the fixed reference signal. The correlated signals are applied to the computer 14 and displayed on a monitor 15 (FIG. 1).

The mechanical strength and structural integrity of hard tissues, such as bone, can be determined by analyzing any correlated signal in terms of ultrasound parameters including the velocity of the ultrasound in the tissue, attenuation and the degree of dispersion of the ultrasound signal while propagating through the tissue. A variable delay gate 23, having a starting position and a width that can be determined by those skilled in art interactively through the monitor 15, limits the range of the correlated output to separate the ultrasound energy propagated along the soft tissues from the ultrasound energy propagated along the hard tissue. The auto-correlated signal and cross-correlated signal can be represented, in the frequency domain, by a fast Fourier transform (FFT) 24 as an approximated power spectrum 25 and cross-spectrum 26, respectively. A digital divider 27 is used to obtain the approximated characteristic frequency response of the bone. The time domain representation of the approximated frequency response of the bone can be obtained through the inverse fourier transforms (IFFT) 28. The characteristic response of the bone both in the frequency domain and in the time domain can then be used to predict the risk of failure.

Figure 4:
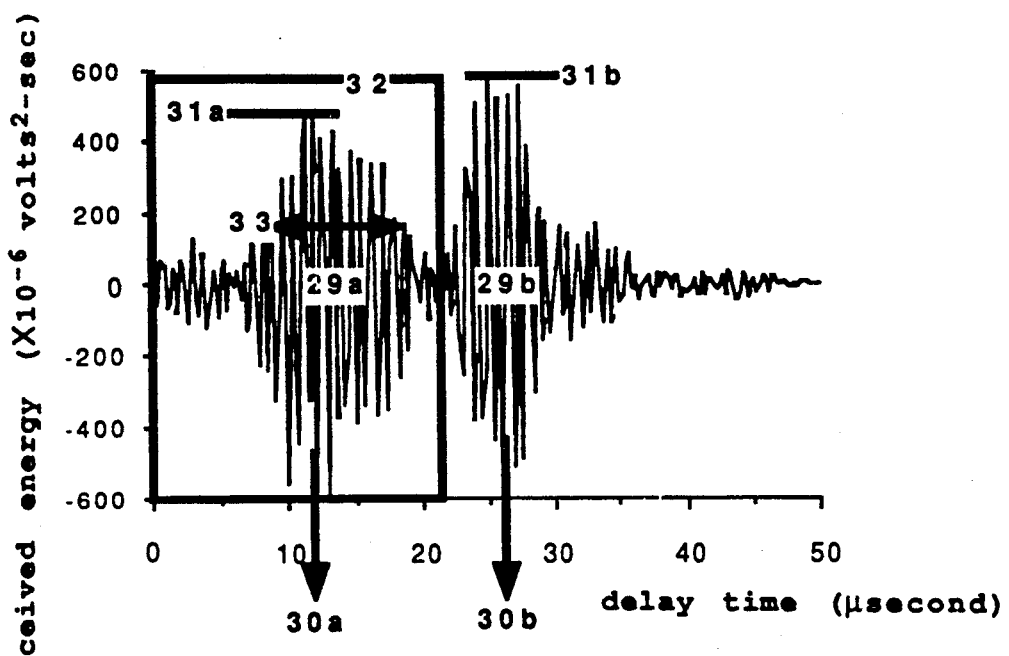
FIG. 4 is a graph illustrating an empirical output of the correlated signal from an in vivo human tibia.

An empirical cross-correlated output from an in vivo human tibia is shown in FIG. 4. To obtain this information the transmitter 2 and the receiver 4 were mounted on an anterior-medial part of the left tibia. To obtain the response illustrated in FIG. 4, two air-backed resonance type piezoelectric transducers (having a resonance frequency of approximately 155 KHz) (such as Dunegan/Endveco Model No. S9204) were used as the transmitter 2 and receiver 4. A received ultrasound signal was amplified to a 70 dB level, and then digitized. The cross-correlated output of the received ultrasound energy shows a clear distinction between ultrasound energy propagated along bone and ultrasound energy propagated along soft tissues. The envelope of distributed energy shown in FIG. 4 has two peaks 29a and 29b. The envelope with peak 29a corresponds to ultrasound energy propagated along bone, and the envelope with peak 29b corresponds to ultrasound energy propagated along soft tissues. The delay time of the envelope with peak 29a was approximately 12.5 μsec. and is represented in FIG. 4 by reference numeral 30a. The delay time of the ultrasound energy propagated along soft tissues was approximately 27 μsec. and is represented in FIG. 4 by reference number 30b. Since the distance between the transducers was measured to be approximately 4.25 cm, the velocity of the ultrasound in the bone and soft tissue was calculated by dividing the distance between the transducers by the delay time for each envelope. The result is that the velocity of the ultrasound in the bone was approximately 3.4 km/sec., and 1.5 km/sec. for the soft tissues.

This measured velocity of ultrasound in both bone and soft tissues agrees well with values reported by others. The maximum ultrasound energy propagated through the bone is approximately $4.65 \times 10^{-4}$ volts²-second, and that propagated through the soft tissues is approximately $6.0 \times 10^{-4}$ volts²-second. The full width at half maximum (FWHM) for the ultrasound energy propagating in the bone is identified by reference numeral 33 in FIG. 4 and is approximately 10 μsec. The variable width gate discussed with reference to FIG. 3 starts at zero sec. and ends at 22 μsec. and therefore has a width represented by reference numeral 32 in FIG. 4. The same variable gate starting position and width is also applied to the auto-correlation function. As a result, only signals within the range of the variable gate signal are used to approximate the characteristic response of the bone being measured.

Figure 5:
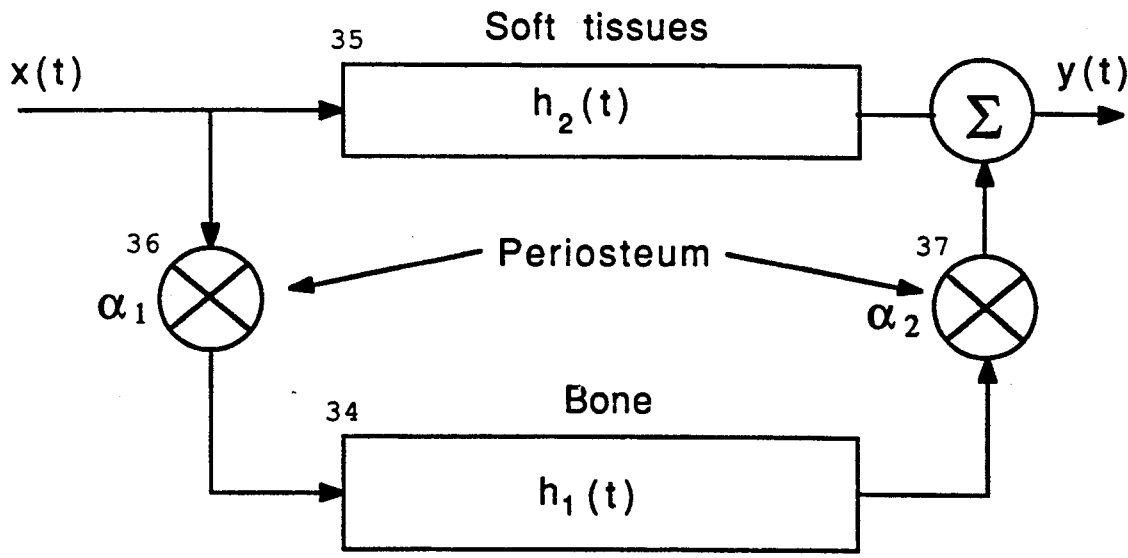
FIG. 5 is a block diagram of a linear approximation model for the bone and soft tissues in ultrasound propagation.

Referring to FIG. 5, a theoretical explanation of the two distinguishable envelope peaks of the cross-correlated output shown in FIG. 4 can be obtained by considering a simplified linear model of ultrasound propagation along the bone and soft tissues. The bone and the soft tissues are simplified to be isotropic and homogeneous materials. The impulse response of a bone 34 is denoted as $h_1(t)$, while that of soft tissues 35 is denoted as $h_2(t)$. To simplify the explanation it is assumed that no considerable time dependent change occurs at the periosteum, denoted by $\alpha_1$ 36 and $\alpha_2$ 37. The fixed reference signal, as mentioned earlier, is established by joining the transmitter 2 and one of the receivers 3, 4 face to face, and is expressed in terms of a convolution as:

$$x(t) = \int_0^\infty x_1(\tau)x_1(t - \tau)d\tau$$

where $x_1(t)$ is the characteristic impulse response of the transducer.

The linear model of FIG. 5 can then be expressed as:

$$y(t) = \alpha_1\alpha_2 \int_0^\infty h_1(\tau_1)x(t - \tau_1)d\tau_1 + \int_0^\infty h_2(\tau_2)x(t - \tau_2)d\tau_2.$$

Then the cross-correlated output has a form:

$$R_{xy}(\tau) = \alpha \int_0^\infty h_1(\tau_1)R_{xx}(t - \tau_1)d\tau_1 + \int_0^\infty h_2(\tau_2)R_{xx}(t - \tau_2)d\tau_2,$$

where $$R_{xx}(\tau) = \lim_{T \to \infty} \frac{1}{T} \int_0^T x(t)x(t + \tau)dt$$

is the autocorrelated output of the reference signal. It is appreciated that the above procedure is essentially a process of accumulation and averaging so that even a very low level input ultrasound can produce a meaningful output, provided that the averaging time is sufficiently long. The $R_{xx}(\tau)$ has the maximum at $\tau=0$. Thus, it is expected that there will be two major peaks arising at $t=\tau_1$ and at $t=\tau_2$. Since ultrasound propagation along bone and soft tissues is actually much more complicated, and since bone and soft tissues are heterogeneous and anisotropic, dispersion of energy peaks around $\tau_1$ and $\tau_2$ of FIG. 4 is expected. Also, since the correlation is a measure of similarity between signals, the degree of dispersion is expected to be smaller in a normal bone than in an abnormal bone. One of the customary methods of measuring the degree of dispersion is the FWHM. This method was employed in the embodiments of the present invention and is a valuable parameter indicating the structural integrity of a bone.

The variable delay gate 23 had a width $\tau_g$, and removes the effects of the soft tissues. The signal provided by the delay gate 23 has the form:

$$R_{xy}(\tau)|_{\tau<\tau_g} = \alpha \int_0^\infty h_1(\tau_1)R_{xx}(t - \tau_1)d\tau_1,$$

which can be expressed in the frequency domain as:

$$S_{xy}(f)|_{bone} = H_1(f)S_{xx}(f)|_{bone},$$

where $$S_{xy}(f)|_{bone} = \int_0^\infty R_{xy}(\tau)|_{\tau<\tau_g}e^{-j2\pi f\tau}d\tau$$

is the approximated cross-spectrum, and $$S_{xx}(f)|_{bone} = \int_0^\infty R_{xx}(\tau)|_{\tau<\tau_g}e^{-j2\pi f\tau}d\tau$$

is the power spectrum. The characteristic frequency response of the bone can be approximated as:

$$|H_1(f)| = \frac{|[S_{xy}(f)|_{bone}]|}{S_{xx}(f)|_{bone}}$$

If ultrasound is propagated through a bone without surrounding soft tissues, the energy of the received ultrasound signal can be calculated by:

$$\text{Energy}(E) = \lim_{T \to \infty} \int_0^T x^2(t)dt = R_{xx}(\tau)|_{\tau=0}.$$

Figure 6:
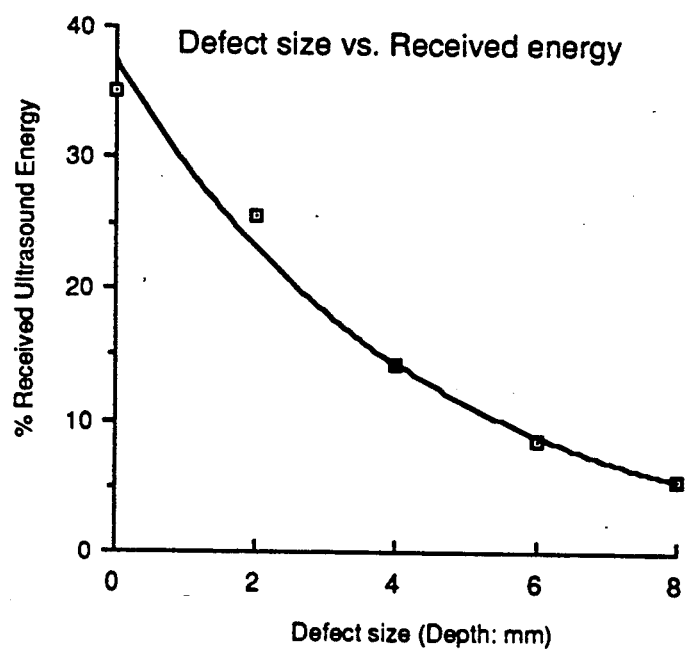
FIG. 6 is a graph illustrating an empirical relation between the received ultrasound energy and simulated defect size.

It should be noted that the calculated energy is proportional to the actual received ultrasound energy by a factor of the inverse of the acoustic impedance. A clear relationship between the received ultrasound energy and simulated defects is shown in FIG. 6. Here, a phantom (plexiglas) was used to simulate a bone, and the defects were introduced by transversely cutting a groove between the transmitter and a receiver. In order to ensure a sufficiently long averaging time, the pulse repetition rate can be set so that the transmitter can be reactivated after the ringing of the transducer due to the previous pulse has completely ceased. As shown in FIG. 6, as the size of the defect increases, the received ultrasound energy decreases.

The ultrasound energy propagated along the bone and along the soft tissues can be expressed respectively as:

$$\text{Energy}(E)|_{bone} = R_{xy}(\tau)|_{\tau=\tau_1},$$

and $$\text{Energy}(E)|_{soft\ tissues} = R_{xy}(\tau)|_{\tau=\tau_2}.$$

As will be apparent from the foregoing description, the present invention provides a novel method of obtaining information about the mechanical strength and the structural integrity of hard connective tissues, insensitive to variations in other tissues. The principles of this invention can be applied to monitor and to diagnose bone disorders.

Although the invention has been described in its preferred embodiment with a certain degree of particularity, it is understood that the present disclosure of the preferred form has been made only by way of example and numerous changes in details of construction and the combination and arrangement of parts may be resorted to without departing from the spirit and scope of the invention as hereinafter claimed.

What is claimed is:

1. A method of measuring in vivo mechanical strength and structural integrity of hard tissues in a body having tissues, soft tissues and skin, comprising the steps of:
   (a) mounting spaced apart ultrasound transducers over the skin and propagating an ultrasound signal from one of said transducers along the hard tissues and surrounding soft tissues;
   (b) establishing a fixed reference signal for the ultrasound transducers;
   (c) receiving the propagated ultrasound signal at another of said transducers;
   (d) sorting the received propagated ultrasound signal according to a relative propagation delay time by correlating the received ultrasound signal with the fixed reference signal;
   (e) determining a velocity, a propagation energy and a degree of dispersion of the ultrasound signal propagated along the hard tissues and the surrounding soft tissues based upon the propagated ultrasound sorting of step (d); and
   (f) relating the velocity, propagated energy and degree of dispersion to the mechanical strength and the structural integrity of the hard tissues.

2. A method according to claim 1, further comprising the step of: establishing an additional reference signal by monitoring the ultrasound signal propagated through a normal part of the hard tissues.

3. A method as claimed in claim 1, wherein step (d) comprises the substep of sorting the received propagated ultrasound signal propagated along the hard tissues and the received propagated ultrasound signal propagated along the soft tissues.

4. A method of measuring mechanical strength and structural integrity of hard tissues in a body having hard tissues and soft tissues, said method comprising the steps of:
   (a) placing an ultrasound transmitter and a first ultrasound receiver over the body with a first distance therebetween;
   (b) placing a second ultrasound receiver over the body at a second distance less than the first distance from the ultrasound transmitter;
   (c) transmitting ultrasound into the body so as to propagate the transmitted ultrasound along the hard tissues and along the soft tissues;
   (d) generating a fixed reference signal by joining the ultrasound transmitter to one of the first and second ultrasound receivers;
   (e) receiving ultrasound propagated along the hard tissues and along the soft tissues at the first ultrasound receiver and at the second ultrasound receiver;
   (f) autocorrelating the received ultrasound signals and cross-correlating the received ultrasound signals with said fixed reference signal;
   (g) extracting the correlated received ultrasound propagated through the hard tissue from the correlated signals; and
   (h) obtaining the approximated frequency response and characteristic response of the hard tissues based upon the extracted ultrasound.

5. A method according to claim 4, wherein step (g) includes gating the received ultrasound in the time domain so as to pass only ultrasound propagated through the hard tissues.

6. A method according to claim 5, wherein step (g) includes a substep of determining the peak and dispersion of the correlated signals.

7. A method according to claim 6, wherein step (h) further includes a substep of performing a fast fourier transform (FFT) on said correlated signals to obtain an approximated power spectrum and an approximated cross spectrum of said correlated signals and performing division between them to obtain the approximated frequency response.

8. A method according to claim 6, wherein step (h) includes a substep of performing an inverse fast fourier transform (IFFT) on the approximated frequency response to obtain the characteristic response of the hard tissues.

9. A method according to claim 4, further comprising the steps of:
   determining a time for said ultrasound transmitted in step (b) to travel between the ultrasound transmitter, the first ultrasound receiver and the second ultrasound receiver; and
   determining the velocity of ultrasound based upon the time delay and the distance between the ultrasound transmitter and the first and second ultrasound receivers.

* * * * *